United States Patent
Murphy (10) Patent No.: US 11,490,914 B2
(45) Date of Patent: Nov. 8, 2022

(54) DUAL OPERATION GRASPING FORCEPS FOR ENDOSCOPE

(71) Applicant: Christopher Murphy, Orlando, FL (US)

(72) Inventor: Christopher Murphy, Orlando, FL (US)

( * ) Notice: Subject to any disclaimer, the term of this patent is extended or adjusted under 35 U.S.C. 154(b) by 43 days.

(21) Appl. No.: 17/065,478

(22) Filed: Oct. 7, 2020

(65) Prior Publication Data

US 2022/0104838 A1   Apr. 7, 2022

(51) Int. Cl.
*A61B 17/221*   (2006.01)
*A61B 17/00*   (2006.01)

(52) U.S. Cl.
CPC ...... *A61B 17/221* (2013.01); *A61B 17/00234* (2013.01); *A61B 2017/00296* (2013.01); *A61B 2017/00358* (2013.01); *A61B 2017/2212* (2013.01)

(58) Field of Classification Search
CPC ............ A61B 17/221; A61B 17/00234; A61B 2017/00296; A61B 2017/00358; A61B 2017/2212
See application file for complete search history.

(56) References Cited

U.S. PATENT DOCUMENTS

| | | | | |
|---|---|---|---|---|
| 549,904 | A * | 11/1895 | Dunbar | A61B 17/44 606/122 |
| 3,794,044 | A * | 2/1974 | Vennard | A61B 17/442 606/123 |
| 4,655,219 | A | 4/1987 | Petruzzi | |
| 5,279,548 | A * | 1/1994 | Essig | A61B 17/42 604/27 |
| 5,667,525 | A | 9/1997 | Ishibashi | |
| 6,093,195 | A | 7/2000 | Ouchi | |
| 6,605,104 | B2 | 8/2003 | Sato et al. | |
| 10,390,848 | B2 | 8/2019 | Taube et al. | |
| 2014/0364866 | A1 | 12/2014 | Dryden et al. | |
| 2017/0215911 | A1 | 8/2017 | Nakajima et al. | |
| 2017/0325829 | A1 | 11/2017 | Chae | |
| 2019/0159798 | A1 | 5/2019 | Saleh | |

\* cited by examiner

*Primary Examiner* — Mohamed G Gabr
(74) *Attorney, Agent, or Firm* — Jason T. Daniel, Esq.; Daniel Law Offices, P.A.

(57) ABSTRACT

A dual operation grasping forceps for use with an endoscope includes an elongated tube having a control mechanism along a first end, and a grasping section along a second end. The grasping section includes a plurality of resilient wire members each having a loop along a distal end. A cable is positioned through the loops to form a circular or triangular shape snare. The grasping members are independently connected to the control mechanism by a first operating wire, and the cable is independently connected to the control mechanism by a second operating wire. The control mechanism selectively moves the grasping section between a retracted position, an extended position and a closed position.

19 Claims, 8 Drawing Sheets

DUAL OPERATION GRASPING FORCEPS FOR ENDOSCOPE

TECHNICAL FIELD

The present invention relates generally to medical devices, and more particularly to a dual operation grasping forceps for endoscopically retrieving foreign objects from a living body.

BACKGROUND

The statements in this section merely provide background information related to the present disclosure and may not constitute prior art.

There are many types of known endoscopic tools or tips for finding, grasping and recovering a foreign object and/or cellular tissue from a living body. With particular emphasis on foreign body recovery, the most commonly utilized instrument is called a grasping forceps which are used in conjunction with an endoscope.

Figure 1A:
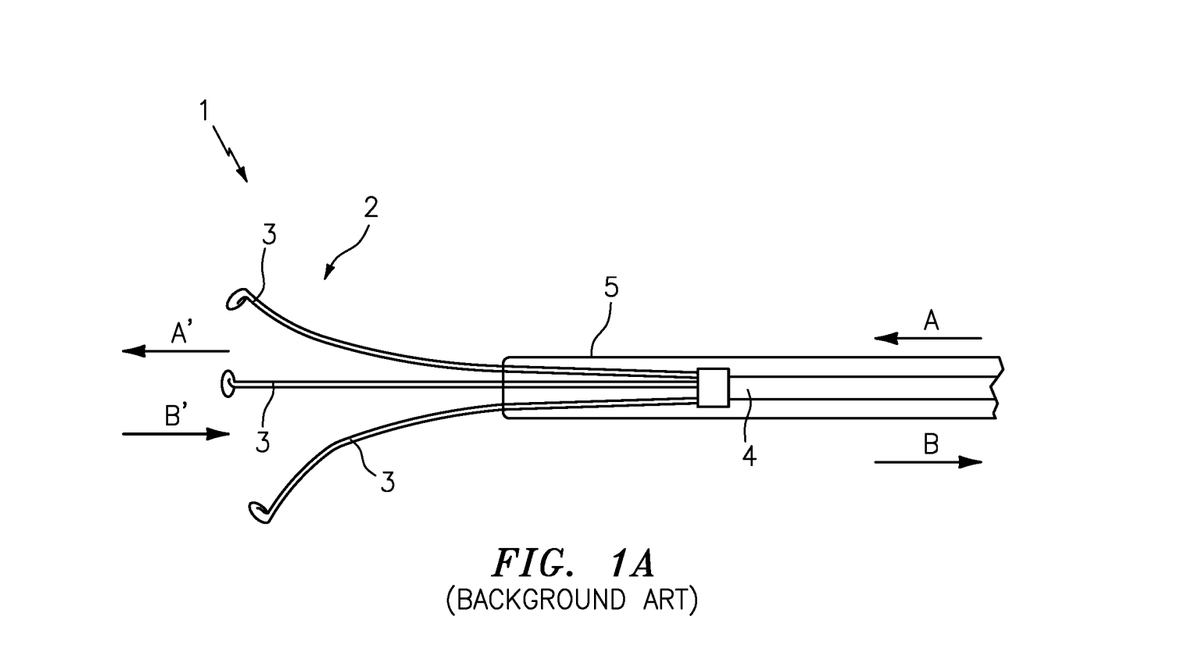
FIG. 1A shows a traditional grasping forceps in accordance with background art.
Figure 1B:
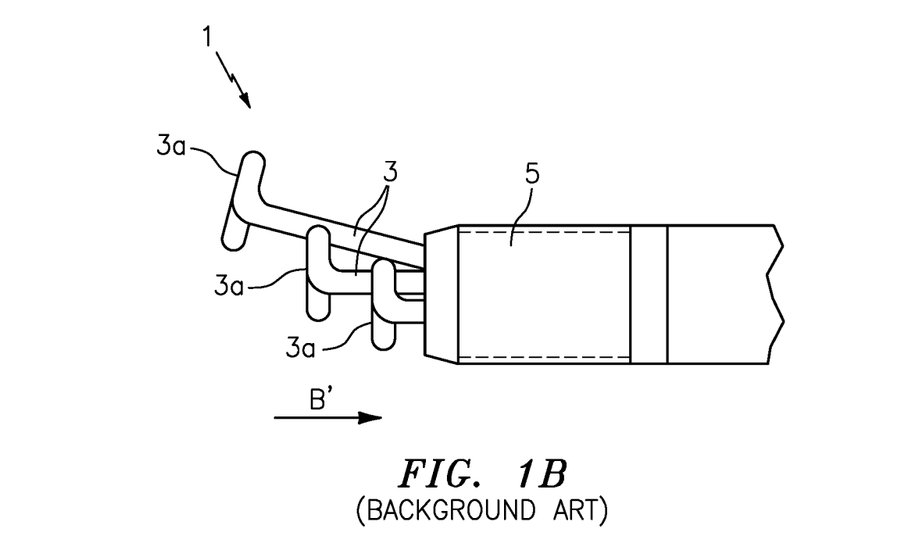
FIG. 1B shows a traditional grasping forceps in accordance with background art.

As shown at background FIGS. 1A and 1B, a typical grasping forceps 1 comprises an elastic grasping section 2 having a plurality of resilient grasping members 3 that are connected to the leading end of an operating wire 4 that is positioned within an insertion tube 5. When an operator moves the operating wire 4 in a first direction (arrow A), the resilient grasping section 2 is pushed away from the leading edge of the insertion tube 5 (arrow A'), and the grasping section 2 spreads outward from the center axis of the tube owing to the elastic restoring forces of the respective grasping members 3. Conversely, when an operator moves the operating wire in a second direction (arrow B), the resilient grasping section 2 contracts as the grasping members are pulled toward and within the leading edge of the insertion tube 5 (arrow B').

When used to retrieve a foreign body, the concept is to position the object within the center of the grasping section 2 and then close the grasping members 3 about the object and remove the same. However, because the wire diameter of each of the resilient grasping members is, by necessity, extremely thin, each wire is unable to independently impart very much force onto the object being retrieved. Indeed, the majority of the grasping force applied from the grasping members to the foreign object come from the tensile strength of the tube 5 itself, as the grasping members are retracted within the tube.

Unfortunately, this design results in several practical drawbacks, as it is extremely difficult to keep the foreign object within the grasping section 2 while closing the grasping members. This is because as the operator attempts to close the members 3 about the foreign object, the operating wire 4 is simultaneously pulling the grasping members 3 toward the tube 5 and away from the foreign object. As such, the operator must constantly move the entire forceps in order to attempt to counteract the movement of the grasping members so as to keep the members about the object.

Moreover, to prevent tissue damage caused by the forceps, the distal ends of the grasping members 3 cannot be sharp. As a result, the grasping members typically comprise a bulbus knob, or other rounded surface which has a tendency to slip off of foreign objects that are smooth and/or have few hard edges.

This design coupled with adverse movement and the low grasping force of the grasping members drastically increases the time and the number of attempts an operator must make in order to successfully remove a foreign object from a patient. As a result, the patient undergoing the procedure is exposed to greater discomfort and/or risk of complication with each passing minute.

Accordingly, it would be beneficial to provide a dual operation grasping forceps for an endoscope that does not suffer from the drawbacks described above.

SUMMARY OF THE INVENTION

The present invention is directed to a dual operation grasping forceps for use with an endoscope. One embodiment of the present invention can include an elongated tube having a control mechanism along a first end, and a grasping section along a second end. The grasping section can include a plurality of resilient members that are independently connected to the control mechanism by a first operating wire. The grasping members can be selectively moved between a retracted position and an extended position by the first operating wire.

In one embodiment, each of the grasping members can include a loop along a distal end, and a cord can be positioned through each of the loops to form a generally circular-shaped snare. One end of the cord can be connected to a second operating wire that is independently connected to the control mechanism.

In one embodiment, the cord can be selectively tightened so as to transition the grasping members to a closed position. When in the closed position, the distal ends of the grasping members are not moved toward the tube.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Definitions

As described herein, a "section" means a series of identified physical components which are linked together and/or function together to perform a specified function.

FIGS. 2-6 illustrate one embodiment of a dual operation grasping forceps 10 that are useful for understanding the inventive concepts disclosed herein. In each of the drawings, identical reference numerals are used for like elements of the invention or elements of like function. For the sake of clarity, only those reference numerals are shown in the individual figures which are necessary for the description of the respective figure.

Figure 2:
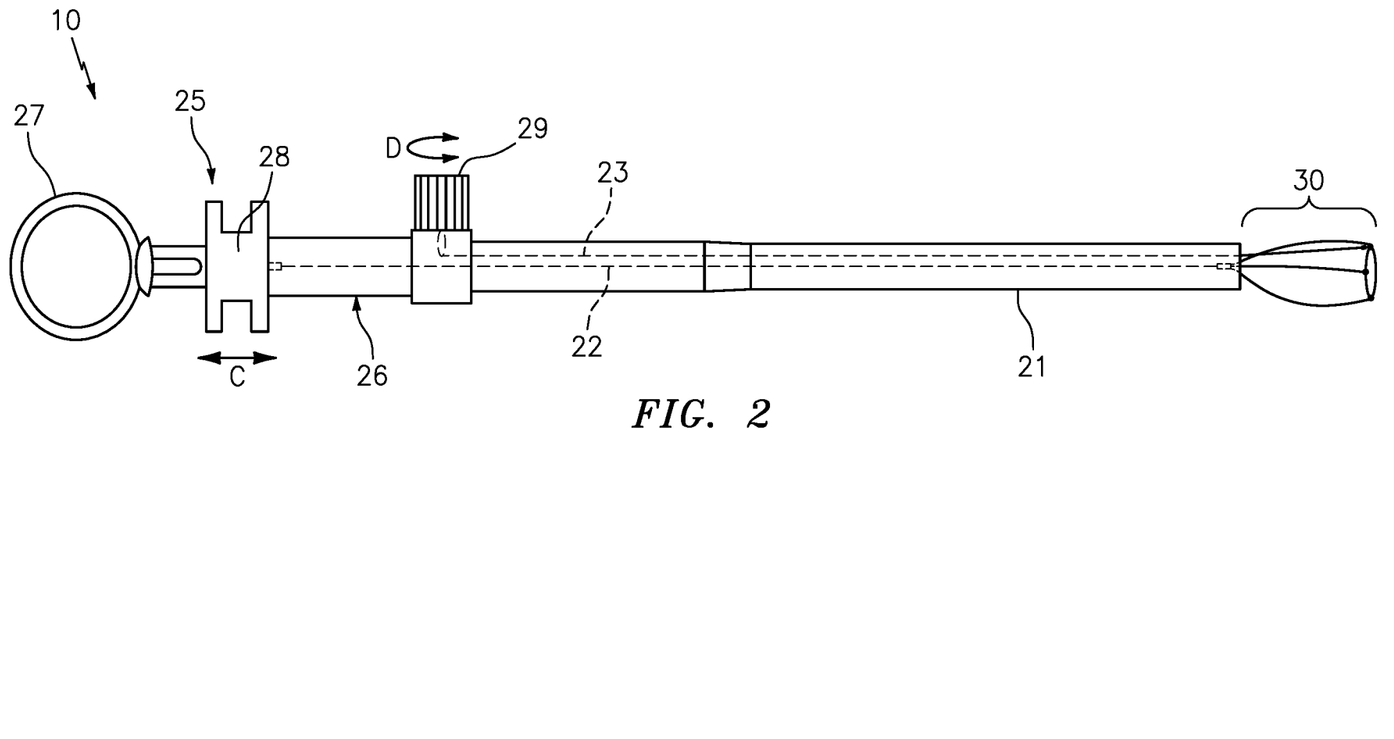
FIG. 2 is a side view of a dual operation grasping forceps, in accordance with one embodiment of the invention.

As shown at FIG. 2, one embodiment of the forceps 10 can include an elongated insertion tube 21 having a first operating wire 22 and a secondary operating wire 23 positioned therein. Each of the operating wires 22 and 23 being in communication with a dual grasping section 30 that is positioned along the distal end of the insertion tube 21.

A control mechanism 25 can be positioned along the proximal end of the insertion tube and can function to selectively operate each of the wires 22 and 23 along the axial direction of the insertion tube. In one embodiment, the control mechanism 25 can include a main body 26 having a fixed gripping surface such as the illustrated thumb loop 27 along the base end of the main body, a lever 28 that slidingly attached to the main body, and a knob 29 that is rotationally attached to the main body.

In this structure, the first operating wire 22 can be moved along the axial direction in the tube 21 by operating the sliding lever 28 in a direction C, whereas the secondary operating wire 23 can be moved along the axial direction in the tube 21 by rotation of the knob 29 in a direction D.

Although described above as including a sliding lever and knob to control the operation of the first and secondary wires, this is for illustrative purposes only. To this end, any number of other objects and arrangement of components are contemplated that are capable of controlling the movement and operation of the wires 22 and 23 in the manner herein described.

For example, in another embodiment, the knob 29 can be positioned on the sliding lever 28. When so positioned, movement of the sliding lever can function to move both the first and secondary operating wires 22 and 23. Such a feature being advantageous for ensuring the below described cord 35 does not remain in an expanded position when the grasping members are contracted.

Figure 3A:
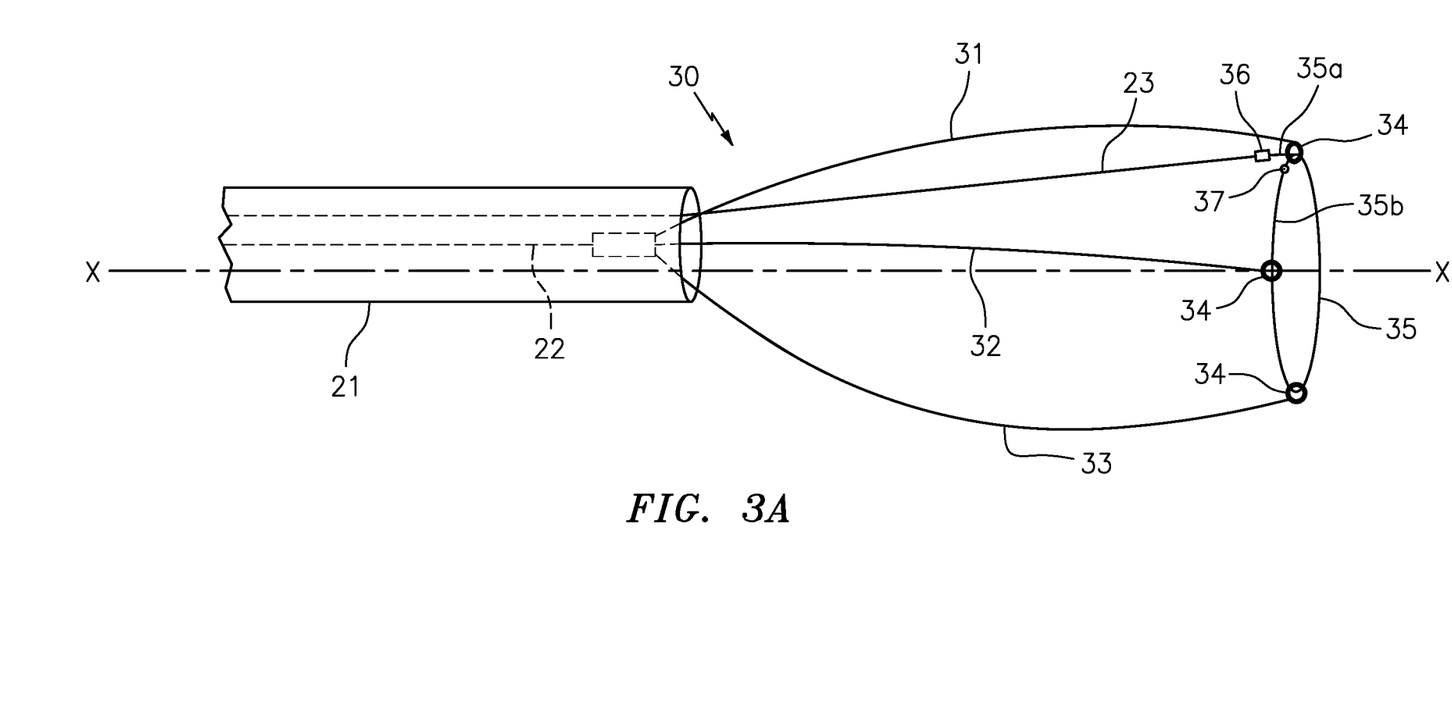
FIG. 3A is a side view of the grasping section of the dual operation grasping forceps in the expanded position, in accordance with one embodiment of the invention.

FIG. 3A illustrates one embodiment of the grasping section 30 in the expanded position. As shown, the section 30 can include a plurality of resilient grasping members 31, 32 and 33 that are each connected to the distal end of the first operating wire 22. In one embodiment, each of the grasping members 31-33 can be constructed from an elastic stainless steel wire or a spring stainless steel wire, for example, that is shaped so as to flex outward from the center axis X of the grasping section and/or distal end of the insertion tube. Although shown and described as being constructed from a particular material and having three distinct grasping members, other embodiments are contemplated wherein the device 10 can be constructed from any number of other materials, and can include a greater number or a fewer number of grasping members without undue experimentation.

To this end, the construction and operation of the first wire-connected components such as the grasping members 31-33, the first operating wire 22, and the insertion tube 21, among others, for example, can be modeled after or can be identical to the construction and operation of the grasping forceps described in U.S. Pat. No. 6,605,104 to Sato, the contents of which are incorporated herein in their entirety by reference.

In one embodiment, each of the resilient grasping wires 31-33 can include a ring/loop 34 along their distal ends. In the preferred embodiment, a cord 35 can be routed through each of the loops 34, and can be connected to the secondary operating wire 23 at a first end 35a by a connector 36. Likewise, the second end of the cord 35b can be connected to one of the loops 34 via a second connector 37.

As described herein, connectors 36 and 37 can each include, comprise or consist of the same or any number of different components that are capable of securing two objects together in either a permanent or removable manner. Several nonlimiting examples include, but are not limited to welds, brazing, adhesives, couplers, and/or formations of materials (e.g., joining the materials through the tying of a knot).

In one embodiment, connector 36 can include a size that is greater than the opening of the loop 34, so as to prevent the cord 35 from expanding beyond the preferred diameter formed by the grasping members of about 20 mm. Such a feature also functions to prevent the cord from becoming loose and inadvertently engaging or snagging an unintended object such as living tissue, for example.

In one embodiment, the cord 35 can be constructed from a malleable strand of stainless steel, for example, and can include a roughened/non-smooth surface formed by grooves, protrusions or braiding, for example. Such a surface advantageously functioning to provide greater traction between the cord 35 and a foreign object being snared by the cord, as described below. Of course, other embodiments are contemplated wherein the cord includes any number of other construction materials, shapes, sizes and surfaces.

Figure 3B:
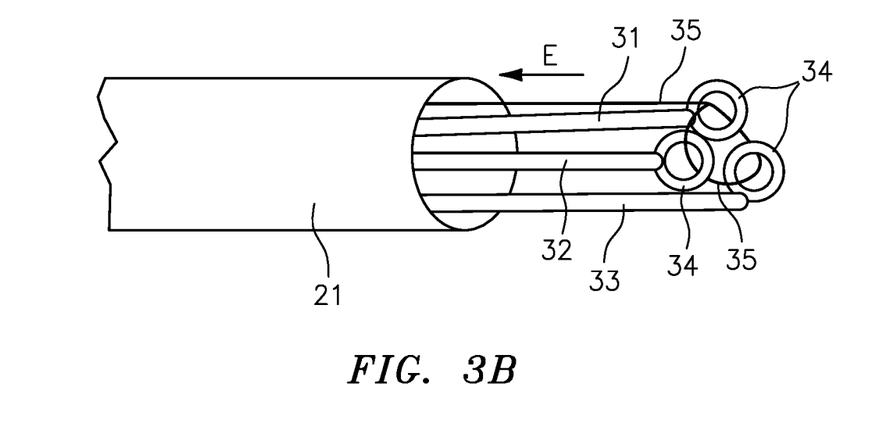
FIG. 3B is a side view of the grasping section of the dual operation grasping forceps in the closed position, in accordance with one embodiment of the invention.

FIG. 3B illustrates one embodiment of the grasping section 30 of the dual operation forceps 10 in the closed position. The grasping section can transition to the closed position via actuation of the knob 29 which causes a pulling force E onto the cord 35. As the cord is pulled toward the tube 21, each of the grasping members are pulled together toward the center axis as the diameter of the cord reduces.

However, this action does not cause the grasping members 31-33 themselves to move laterally toward the end of the tube.

Figure 3C:
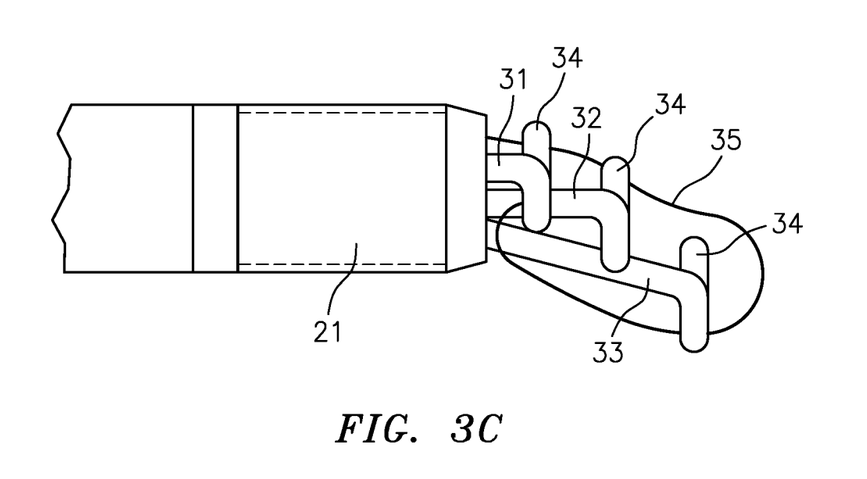
FIG. 3C is a side view of the grasping section of the dual operation grasping forceps in the retracted position, in accordance with one embodiment of the invention.

FIG. 3C illustrates one embodiment of the grasping section 30 of the dual operation forceps 10 in the retracted position wherein both the cord 35 and grasping members are positioned within or adjacent to the distal end of the tube 21.

Although described above as including a separate operating wire 23 and cord 35 that are joined by a connector 36, other embodiments are contemplated wherein the operating wire and cord are constructed as a unitary element, such as a single elongated strand of wire, for example. Additionally, although not specifically illustrated, any number of additional components may be provided within the insertion tube 22 and/or along one or more of the grasping members which can function to align, route or otherwise guide the secondary operating wire 23 to the cord 35.

Figure 4:
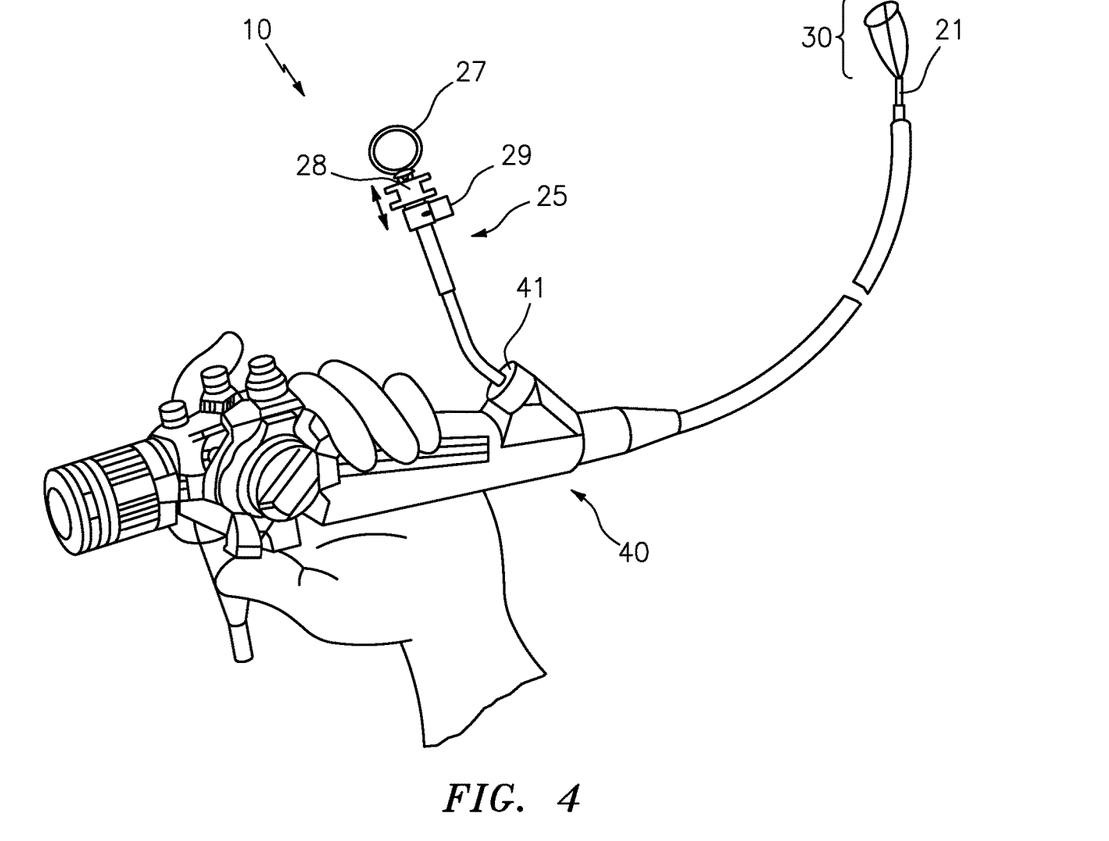
FIG. 4 is a perspective view of the dual operation grasping forceps in operation, in accordance with one embodiment of the invention.
Figure 5:
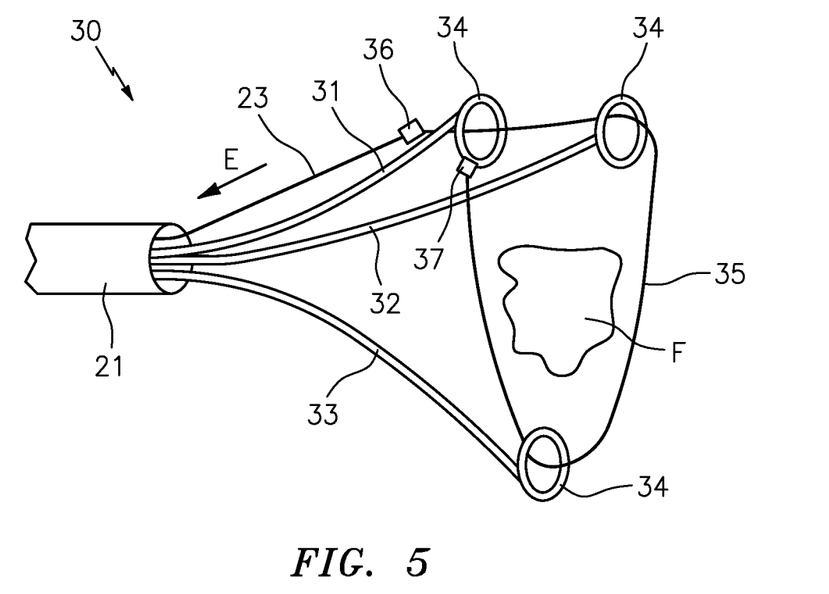
FIG. 5 is a perspective view of the grasping section of the dual operation grasping forceps in operation and in the expanded position, in accordance with one embodiment of the invention.
Figure 6:
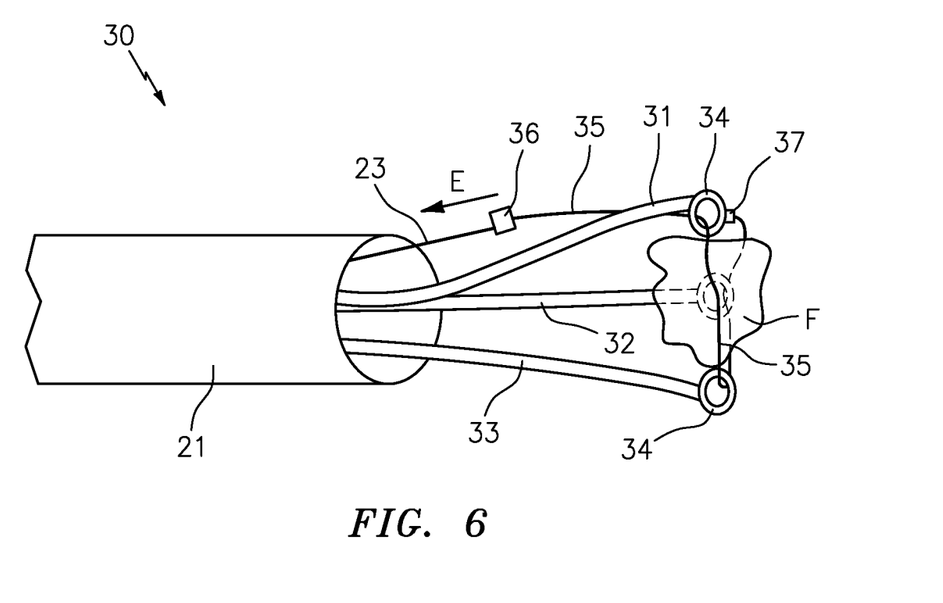
FIG. 6 is a perspective view of the grasping section of the dual operation grasping forceps in operation and in the closed position, in accordance with one embodiment of the invention.

FIGS. 4-6 illustrate one embodiment of the forceps 10 in operation. As shown, the tube 21 of the forceps can be positioned within the instrument channel 41 of an endoscope 40 and ultimately guided to an appropriate location within a patient. When so positioned, the operator can slide the lever 28 forward, in order to expand the grasping members 31-33 and the tether 35 to the expanded position.

As shown at FIG. 5, the operator can next move the grasping section 30 so as to position a foreign object F, polyp or other target material within the expanded circular snare area formed by the cable 35 and grasping members. When so positioned, the operator can twist the knob 29 so as to impart a pulling force E onto the secondary operating wire 23.

As shown at FIG. 6, this pulling force causes the grasping section to transition to the closed position wherein diameter of the cable 35 shrinks until each of the grasping members are in contact with the foreign object, and the cable is completely encircling a portion of the foreign object F. Importantly, however, this movement does not cause lateral movement of the grasping members, and therefore does not result in the grasping members being pulled away from the foreign object F while trying to engage the same.

Finally, once the object is secured as described above, the operator can then retract the grasping members using the lever 28, which will impart an additional grasping force onto the object F and can remove the same from the patient's body. In addition to the above described sequence, it is noted that the inventive forceps 10 can also be used in a traditional manner wherein an object can be retrieved using only the grasping members themselves, or through a combination of both sequences.

Figure 7:
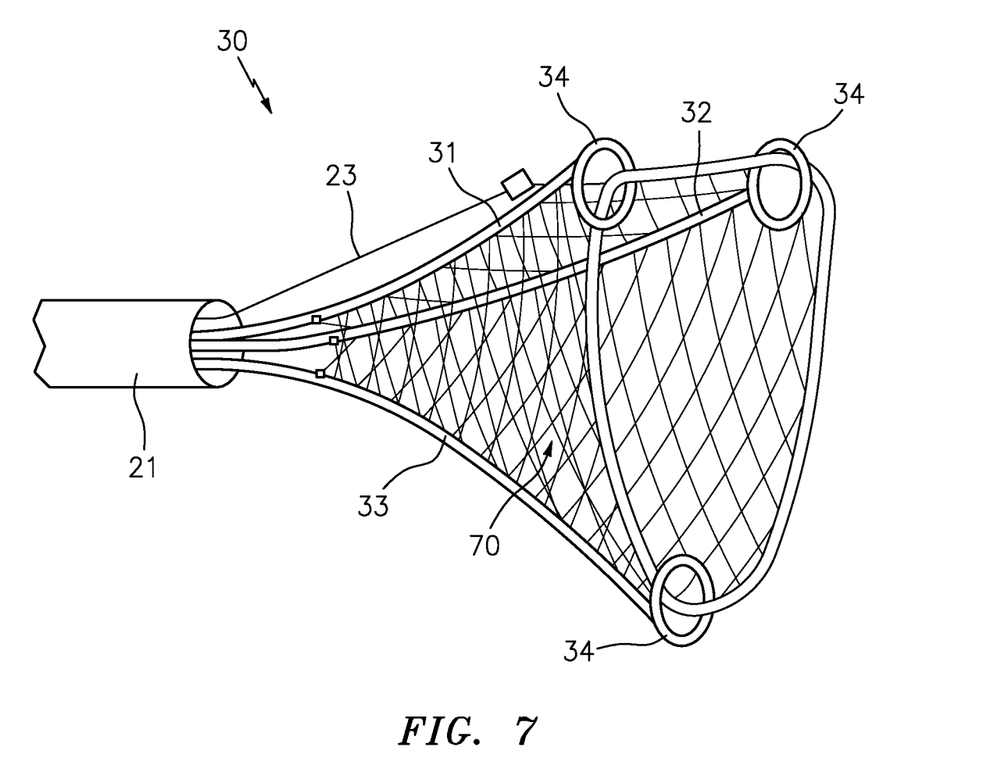
FIG. 7 is a perspective view of the grasping section of the dual operation grasping forceps, in accordance with one embodiment of the invention.

Although described above as including a single cord 35 that is positioned along the distal ends of the grasping members, other embodiments are also contemplated wherein the cord is positioned at other locations along or within the grasping members. Additionally, FIG. 7 illustrates one embodiment of the grasping forceps 10 that includes a net/mesh material 70 that is positioned between each of the plurality of grasping members 31-34. As shown, the net 70 can be in communication with the cord 35 along a front end so as to form a generally cone-shaped chamber extending from the net 35 toward the front end of the tube 21. The net can expand and contract in the same manner described above, and can increased functionality to the device.

As described herein, one or more elements of the dual operation grasping forceps 10 can be secured together utilizing any number of known attachment means. Moreover, although the above embodiments have been described as including separate individual elements, the inventive concepts disclosed herein are not so limiting. To this end, one of skill in the art will recognize that one or more individually identified elements may be formed together as one or more continuous elements, either through manufacturing processes, such as welding, casting, or molding, or through the use of a singular piece of material milled or machined with the aforementioned components forming identifiable sections thereof.

As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Likewise, the terms "consisting" shall be used to describe only those components identified. In each instance where a device comprises certain elements, it will inherently consist of each of those identified elements as well.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A dual operation grasping forceps for an endoscope, comprising:
   an elongated flexible insertion tube having a first end and a second end;
   a controller that is positioned along the first end of the insertion tube;
   a grasping section that is positioned along the second end of the insertion tube, said grasping section including a plurality of resilient grasping members each having a loop along a distal end;
   a cord that is positioned through the loop of each of the grasping members,
   a first operating wire that is connected to the controller along a first end, and the plurality of grasping members along a second end; and
   a second operating wire that is connected to the controller along a first end, and the cord along a second end,
   wherein the insertion tube is configured to be positioned within an instrument channel of an endoscope,
   wherein the grasping section is configured to transition between an expanded position, a closed position, and a retracted position, and wherein the controller is configured to control an operation of the grasping section.

2. The forceps of claim 1, wherein in the expanded position, the distal ends of the plurality of grasping members are extended laterally away from the second end of the insertion tube, and the distal ends of the grasping members are spread outward from a center axis of the second end of the insertion tube.

3. The forceps of claim 2, wherein in the expanded position, the cord forms a generally circular shape.

4. The forceps of claim 1, wherein in the closed position, the distal ends of the plurality of grasping members are extended laterally away from the second end of the insertion tube, and the distal ends of the grasping members are not spread outward from a center axis of the second end of the insertion tube.

5. The forceps of claim 4, wherein in the closed position, the cord is pulled taut between the distal ends of the grasping members.

6. The forceps of claim 1, wherein in the retracted position, the distal ends of the plurality of grasping members are positioned against the second end of the insertion tube and the distal ends of the grasping members are not spread outward from a center axis of the second end of the insertion tube.

7. The forceps of claim 6, wherein in the retracted position, the cord is pulled taut between the distal ends of the grasping members.

8. The forceps of claim 1, wherein the cord includes a roughened non-smooth outer surface.

9. The forceps of claim 8, wherein the roughened non-smooth surface is formed by a plurality of grooves and protrusions along the outer surface.

10. The forceps of claim 1, wherein the controller includes a sliding lever that controls an operation of the first operating wire.

11. The forceps of claim 10, wherein the controller includes a rotational knob that controls an operation of the second operating wire.

12. The forceps of claim 10, wherein the cord is connected to the second end of the second operating wire by a connector.

13. The forceps of claim 12, wherein in the expanded position, the cord forms a generally circular shape, and
said connector functions to limit a diameter of the circular shape to a maximum diameter.

14. The forceps of claim 13, wherein the maximum diameter is 20 mm.

15. The forceps of claim 12, wherein the cord includes a first end that is connected to the connector, and a second end that is connected to the loop of one of the plurality of grasping members.

16. The forceps of claim 15, wherein the connector includes a size that is larger than an opening of the loop of each of the plurality of grasping members.

17. The forceps of claim 16, wherein in the expanded position, the cord forms a generally circular shape, and
said connector functions to limit a diameter of the circular shape to a maximum diameter.

18. The forceps of claim 1, further comprising:
a net that is positioned between each of the plurality of grasping members.

19. The forceps of claim 18, wherein a distal end of the net is connected to the cord.

* * * * *